(12) United States Patent
Atlan

(10) Patent No.: US 11,219,508 B2
(45) Date of Patent: Jan. 11, 2022

(54) PALATAL EXPANSION DEVICE (PALATAL EXPANDER)

(71) Applicant: David Atlan, Franconville-la-Garenne (FR)

(72) Inventor: David Atlan, Franconville-la-Garenne (FR)

( * ) Notice: Subject to any disclaimer, the term of this patent is extended or adjusted under 35 U.S.C. 154(b) by 0 days.

(21) Appl. No.: 16/091,652

(22) PCT Filed: Apr. 5, 2017

(86) PCT No.: PCT/FR2017/050801
§ 371 (c)(1),
(2) Date: Oct. 5, 2018

(87) PCT Pub. No.: WO2017/174929
PCT Pub. Date: Oct. 12, 2017

(65) Prior Publication Data
US 2019/0159872 A1    May 30, 2019

(30) Foreign Application Priority Data

Apr. 8, 2016    (FR) ...................................... 1653141

(51) Int. Cl.
*A61C 7/10*    (2006.01)
*A61B 17/66*    (2006.01)
(52) U.S. Cl.
CPC .............. *A61C 7/10* (2013.01); *A61B 17/663* (2013.01)
(58) Field of Classification Search
CPC .. A61C 7/10; A61C 7/146; A61C 7/22; A61C 7/02; A61C 19/003; A61B 17/663;
(Continued)

(56) References Cited

U.S. PATENT DOCUMENTS 3,977,082 A * 8/1976 Siatkowski .............. A61C 7/10
                                                            433/7
4,408,989 A * 10/1983 Cleary ..................... A61C 7/00
                                                            433/7
(Continued)

FOREIGN PATENT DOCUMENTS

DE          10234376 A1    2/2004
FR           2742039 A1    6/1997
KR      1020090120895 A   11/2009

OTHER PUBLICATIONS

International Search Report for corresponding application PCT/FR2017/050801 filed Apr. 5, 2017; dated Jul. 5, 2017.
(Continued)

*Primary Examiner* — Nicholas D Lucchesi
*Assistant Examiner* — Mirayda A Aponte
(74) *Attorney, Agent, or Firm* — Cantor Colburn LLP

(57) ABSTRACT

An orthodontic device having at least one first bearing element configured for bearing on the left-hand side of an upper jaw of a patient to be treated, at least one second bearing element configured for bearing on the right-hand side of the jaw and a central actuator for modulating a distance between the bearing element in order to expand the palate of the patient. The device further includes a mechanical rotary link between the actuator and the first bearing element and a mechanical rotary link between the actuator and the second bearing element in order to allow geometric adjustment while the device is being fitted in the mouth of the patient, at least in the vertical direction, the anterior-posterior direction, or the transverse direction.

9 Claims, 10 Drawing Sheets

(58) Field of Classification Search
CPC ......... A61B 17/66; A61B 17/60; A61B 17/58; A61B 17/56
USPC .................................. 433/7, 3, 22, 2, 20, 8
See application file for complete search history.

(56) References Cited

U.S. PATENT DOCUMENTS

| | | | | |
|---|---|---|---|---|
| 5,645,422 | A * | 7/1997 | Williams | A61C 7/10 433/7 |
| 6,358,255 | B1 * | 3/2002 | Testa | A61B 17/663 433/7 |
| 2002/0018978 | A1 * | 2/2002 | Triaca | A61B 17/663 433/7 |
| 2013/0252195 | A1 * | 9/2013 | Popat | A61C 7/10 433/24 |

OTHER PUBLICATIONS

EP Examination Report dated Apr. 16, 2021 re: Application No. 16 726 668.3-1105, pp. 1-5.

* cited by examiner

PALATAL EXPANSION DEVICE (PALATAL EXPANDER)

TECHNICAL FIELD

The disclosure falls within the field of orthodontics, dental-facial orthopedics (dfo) and maxillofacial surgery, in particular human.

BACKGROUND

Palatal expansion, or palatal expander, devices are known, used to widen the palate and the upper jaw, in children, adolescents, or in some cases adults. They are used when the upper jaw is too narrow. They make it possible to enlarge the structure made up of the two maxillary bones in the transverse direction, and to widen the median palatal sutures and the incisive sutures. A widening or expansion of the sutures is sought through a skeletal effect and a widening of the dental arch through dento-alveolar effect, depending on the bearing type, pressure type and age of the patient.

In these devices, a central jack is activated by prescription in order to perform the centripetal bone distraction or expansion. The jack may be integrated into a removable plate, or glued on the teeth using thermoformed troughs or rings. The system uses bone supports on the maxillary bones, or dental supports on the molars, the premolars and the canines.

The entire device is custom made by a prosthetics laboratory.

FIG. 1 shows such a known palatal expansion device, presented as an example. It includes bearing parts 1 and 2, here each made up of a ring that grips a molar on each side of the palate and bears on the gripped molar and the adjacent teeth via proximal or distal bearing extension bars. It also includes a central jack 3. The central jack 3 is adjustable to provide a transverse separation between the two rings 1 and 2. Rigid rods 4, 5 and 6, 7 provide the fixed connection between the central jack 3 and the bearing parts 1 and 2, while allowing the device to be as minimally bothersome and as discreet as possible. These rods provide the connections between the central jack and the teeth, but also provide the rigidity, the transmission and the distribution of forces necessary for the desired movements.

Materials such as stainless steel or titanium can be used, as well as other biocompatible materials, including compatible alloys.

FIG. 2 shows the device placed in the mouth of a patient, who wears it for several weeks or several months. As the device produces its effects, the jack is adjusted (or "activated") to maintain a separating force, thus gradually increasing the distance between the two parts of the jaw and/or the various bones. The adjustment is done by rotating a central screw of the jack that causes the transverse expansion. The screw is rotated with an appropriate tool, such as a key 8. When the desired expansion is achieved, the device is kept in place during a certain period to consolidate the treatment, then it is removed.

EP09190207 discloses a palatal expansion device, using a concave receiving element for each arm and associated with a fastening surface to be associated with the corresponding tooth, the receiving element being coupled to the arm and by mechanical interference or narrowing, or spot welding, or laser welding, or adhesion means.

US 20130252195 discloses a palatal expansion device in a kit with the use of arms with different geometries to be chosen.

Despite the existing devices, there is currently no truly flexible solution allowing quick placement without using a prosthetist, and that is adaptable, through a presentation in a kit with placement on each patient without requiring taking imprints and spending considerable time in a prosthetist's office.

BRIEF SUMMARY

To resolve the problems thus identified, proposed is an orthodontic device including at least a first bearing means, for dental, gingival or bone bearing, to bear on the left side of a jaw (or on the left maxillary bone or on the left mandibular bone) of a patient to be treated, at least one second bearing means, for dental, gingival or bone bearing, to bear on the right side of said jaw (or on the right maxillary bone or the right mandibular bone) and a central jack for modulating a separation of said bearing means to widen the palate of said patient, characterized in that the device also includes a means for continuous or discrete angular adjustment, for example a mechanical rotation link, between the jack and said first bearing means and a means for continuous or discrete angular adjustment, for example a mechanical rotation link, between the jack and said second bearing means to allow a geometric adjustment during a placement of the device in the patient's mouth, at least in the vertical direction, the anterior-posterior direction or the transverse direction, for the adaptation of the device to the morphology of the patient, his pathology and the therapeutic resolution of the treated malformation. The geometric adjustment and the placement of the device are adapted to the morphology of the mouth.

Such a system offers great configurability, can be prefabricated, and is easily adjustable and adaptable to each patient. It is adjustable, configurable in the mouth in the chair or outside the mouth, and is fixable, i.e., it is next possible to freeze its position. The system has an articulation that exists solely for the adjustment and that is next counteracted once the placement is finished.

According to various advantageous features,
- the adjustment is possible in the vertical direction, the anterior-posterior direction and the transverse direction;
- the first or second bearing means includes at least a first connecting beam to be placed between the jack and a first tooth, and a second connecting beam to be placed between the jack and a second tooth;
- at least one of the beams is telescoping or at least adjustable lengthwise to allow a geometric adjustment during a placement of the device in the patient's mouth;
- at least one of the beams can be disassembled, the device including at least one replacement beam with a different length to allow a geometric adjustment during a placement of the device in the patient's mouth;
- the device includes a rotating mechanical link at the end of each beam between the beam and the jack;
- it includes a rotating mechanical link at the end of each beam opposite the jack, to be inserted between the beam and the jaw;
- it includes fasteners to be glued on the teeth, by sealing or gluing or mechanical or chemical retention, and bearing connecting means to connect the fasteners to the jack, the device additionally including complementary connecting elements connected to the jack to place the device in the patient's mouth using fasteners;
- it includes fasteners with different sizes and shapes for adaptation to different types of teeth and morphologies;

at least one of the fasteners includes a fragile or weak zone allowing removal by deformation;

the fasteners, several types of which exist based on the significance of the pressure and the type of movement to be applied, bear single outer notches, double outer notches or an outer ball for a nesting connection, or screwing elements for a screwing connection;

the jack is fastened by embedding or any other fastening means on a left support and a right support that are free relative to one another.

Owing to these various features, one has an expansion jack equipped with arms articulated in all three dimensions. The assembly is proposed in a kit, with adjustable parts having different lengths. At the ends of each arm, a fixing system makes it possible to fix the arms on the teeth, while adapting to each tooth, and adapting to the distance and the orientation between the central jack and the tooth. The assembly of the system allows the placement of the device by fine and adaptable gluing where all of the elements are prefabricated and adjusted directly in the patient's mouth. This results in saved time, and comfort for the practitioner and the patient, as well as improved precision.

The disclosure also relates to a method for placing an orthodontic device including a step for forming a first bearing of the device on the left side of the jaw of a patient to be treated, a step for forming a second bearing for the device on the right side of said upper jaw, and a step for modulating the separation between the two jaws by a central jack of the device, characterized in that the placement method additionally includes a step for adjusting an angle between the jack and said first bearing or an angle between the jack and said second bearing to allow a geometric adjustment of the device in the patient's mouth or outside the mouth adapted to the morphology thereof, at least in the vertical direction, the anterior-posterior direction or the transverse direction.

The steps for forming bearings may include placing a support on the jaw and/or positioning the device bearing on the jaw.

BRIEF DESCRIPTION OF THE DRAWINGS

The description will continue in connection with the figures, presented as an illustration.

FIG. 6a shows a detail of the preceding aspect of the disclosure, in a first alternative.

FIG. 6b shows a detail of the preceding aspect of the disclosure, in a second alternative.

FIG. 11a shows the vertical adjustment. FIG. 11b shows the anterior-posterior adjustment. FIG. 11c shows the anterior-posterior adjustment. FIG. 11d shows another option.

DETAILED DESCRIPTION

Figure 1:
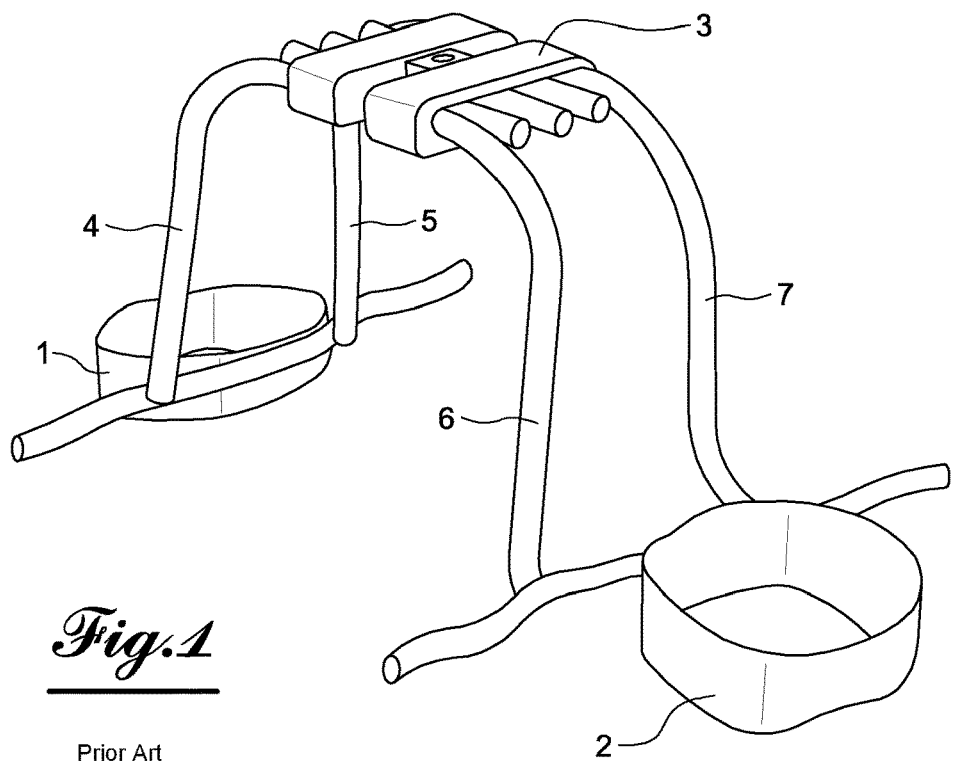
FIG. 1 shows a system according to the prior art.
Figure 2:
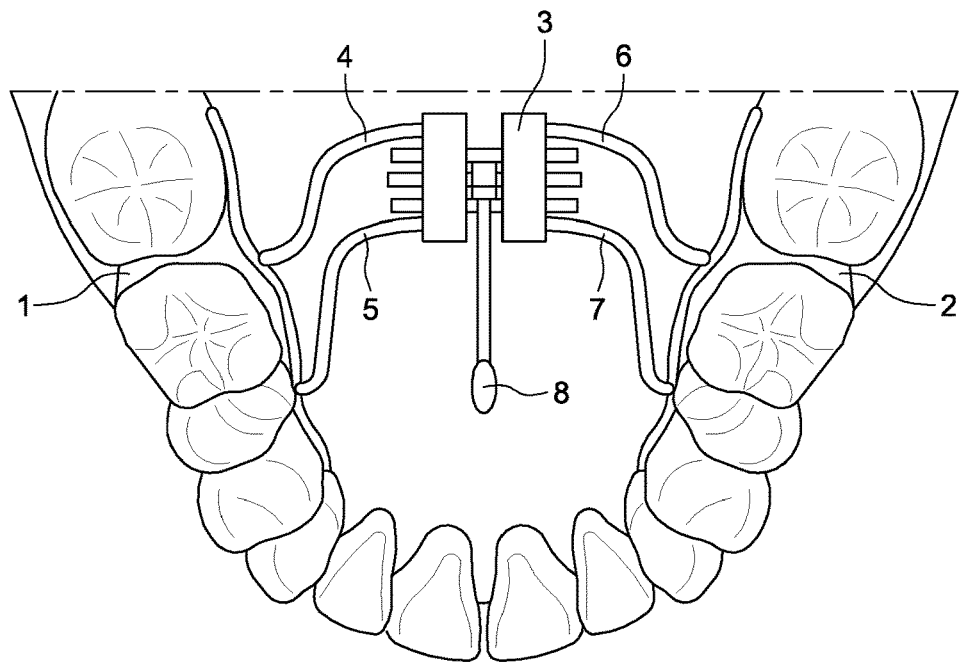
FIG. 2 shows the system of FIG. 1 in position.
Figure 3:
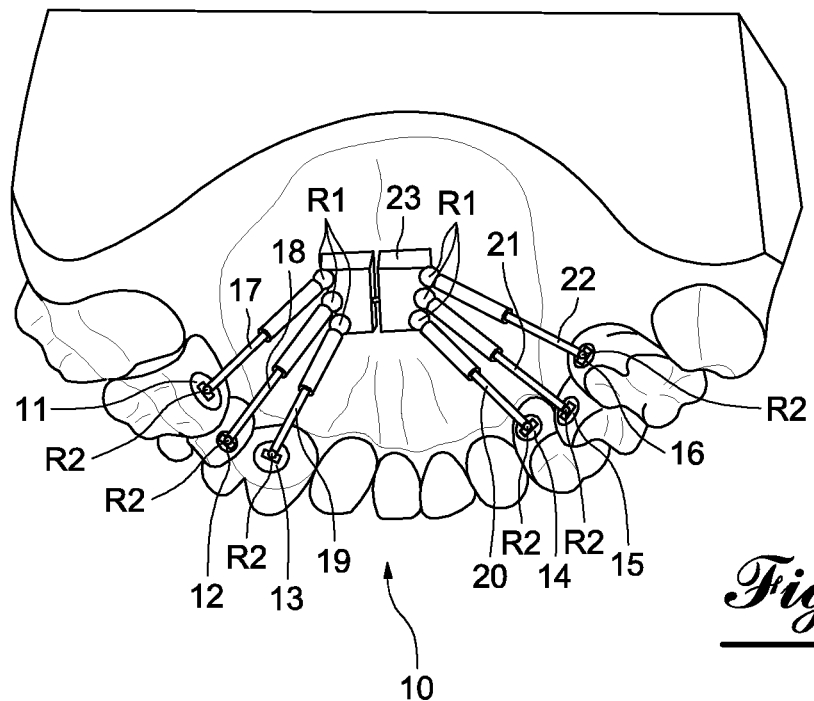
FIG. 3 shows a general view of a system according to the disclosure, during its placement.

In FIG. 3, a palatal expansion system 10 is shown according to the disclosure, placed at the upper jaw of a patient.

The palatal expansion system 10 includes six fixing elements to the teeth 11 to 16, three of which, referenced 11 to 13, are on the teeth on one side of the jaw and the other three of which, referenced 14 to 16, are on the corresponding teeth of the other side of the jaw. The fastening and bearing can be dental, gingival and/or bone-based.

The palatal expansion system also includes six bearing arms (or beams) 17 to 22 each bearing on one of the fixing elements 11 to 16. It also includes a central jack 23. The bearing arms 17 to 22 each connect one of the fixing elements 11 to 16, respectively, to the central jack 23. The bearing arms 17 to 22 are all telescoping arms, or at least arms with adjustable lengths using one or the other of several possible systems: pneumatic jack, telescoping arm, screw pitch, notched arm, etc., able to adapt to various lengths, the values of which may be chosen continuously or discreetly.

Each bearing arm is connected to the central jack by an associated ball joint R1, and to the corresponding element for fixing to the teeth by an associated second ball joint R2.

In FIG. 3, the system is in the placement phase, and the 12 ball joints R1 or R2 are partially or completely free and may therefore allow movements between the jack, the arms and the teeth.

Figure 4:
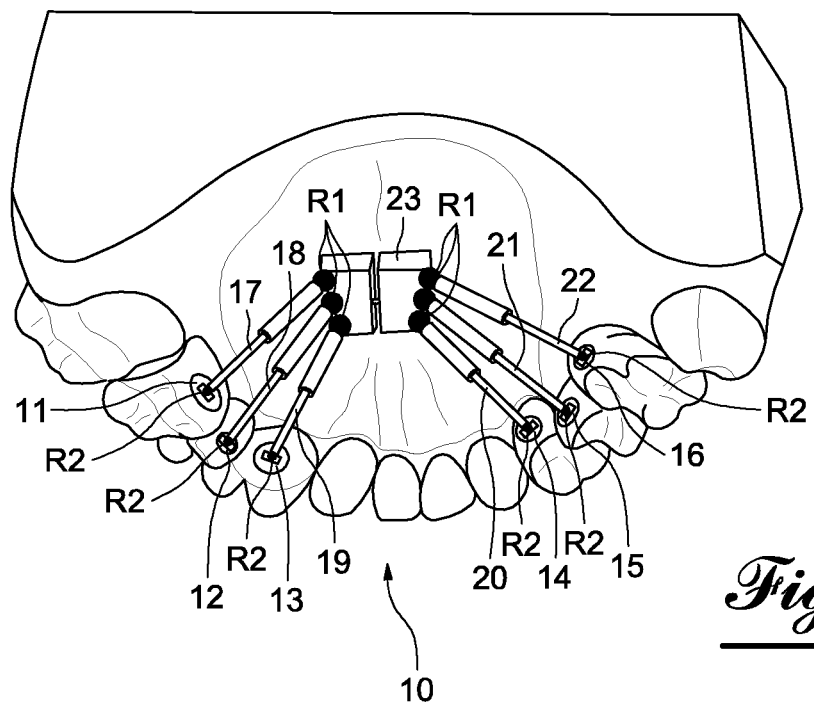
FIG. 4 shows a general view of the system of FIG. 3, once fixed.

FIG. 4 shows the palatal expansion system 10 after stiffening thereof. One or several stiffening elements stiffen the six ball joints R1 connecting the central jack to the arms. Stiffening elements are also placed at the ball joints R2 connecting the arms and the fixing elements to the teeth 11 to 16. The stiffening elements may all be of the same type, or may be different. Different stiffening strategies can be used. They can use a stiffening element integrated into the palatal expansion system 10, for example integrated into the ball joints R1 and R2, or be brought from the outside, such as glue, such as a composite glue, an ionomer glass cement, an IRM sealant (Dentsply brand) or a resin activated by photopolymerization or chemical polymerization.

In one embodiment, once the system is locked, it can be unlocked with an unlocking key or any outside tool. In other embodiments, once the system is locked, it cannot be unlocked, and must therefore, in order to be undone, be in the case of a photopolymerization in order to undo it, it is necessary to break it [sic]. This is for example the case in the case of locking by photopolymerization.

FIG. 5 shows different fixing elements that can be used to fix the arms to the teeth. The fixing is done by connection, in particular clipping, of an element present at the end of the arm, and an element pre-positioned on the side surface of the tooth on the inner side of the mouth (palatal or lingual face of the tooth). These two elements to be clipped are complementary and can have different shapes, which may for example be described as male and female shapes. In the case of a pair of male and female shapes, the male shape may indifferently be on the arm, or fixed to the tooth. The clipping involves a locking shape.

Figure 5A:
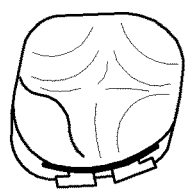
FIG. 5a shows a first aspect of the disclosure, namely fasteners to be placed on the teeth, in a first alternative.

In FIG. 5a, the part fixed to the tooth has two detached shapes separated by a space, and is described as fixing with double male notch 100. Each of the shapes in fact has a space to engage a complementary shape attached to the arm. Said complementary shape is then engaged between the part and the tooth. The two detached shapes are positioned back to back, which justifies the name "inner/outer". The engagement spaces make it possible to jointly propose a system for retaining the complementary part attached to the arm.

Figure 5B:
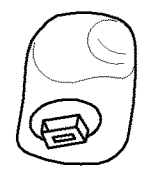
FIG. 5b shows a first aspect of the disclosure, namely fasteners to be placed on the teeth, in a second alternative.

In FIG. 5b, the part attached to the tooth has a single slit and is described as single female attachment notch 101.

Figure 5C:
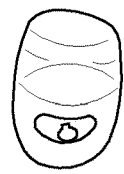
FIG. 5c shows a first aspect of the disclosure, namely fasteners to be placed on the teeth, in a third alternative.

In FIG. 5c, the part attached to the tooth has an outer ball and is described as male attachment ball 102.

Figure 5D:
FIG. 5d shows a first aspect of the disclosure, namely fasteners to be placed on the teeth, in a fourth alternative.

In FIG. 5d, the part attached to the tooth has a double outer notch and is described as double female notch attachment 103.

Figure 6C:
FIG. 6c shows a detail of the preceding aspect of the disclosure, in a third alternative.
Figure 6C:
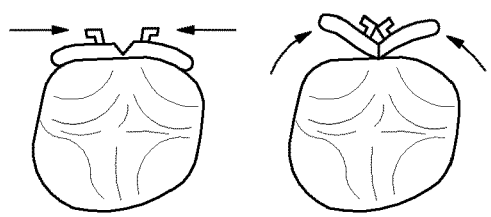

FIG. 6 shows the gluing surface of the fastening elements to the teeth previously discussed. These fasteners have different sizes, curves and shapes to adapt to the different dental morphologies: small size for fastening on incisor or canine, medium for fastening to a premolar, or larger fastening on the molar, as shown in FIG. 6a. In FIG. 6b, an embodiment is shown in which the adhesion surface has a fragile zone to allow easy removal by deformation. The forces needed to deform the placed fastener are shown in the left part of FIG. 6c, and the result on the fastener, in profile view, is shown in the right part of said FIG. 6c: the two parts of the fastener surrounding the fragile part deform, then releasing the tooth.

Figure 6D:
FIG. 6d shows a detail of the preceding aspect of the disclosure, in a fourth alternative.

In FIG. 6d, a medium gluing surfaces shown from different angles: front, top view, profile view and back view. The element is a thin part, curved to marry a tooth surface, and having a grated inner face to allow the mechanical retention of the glue. There is then glue on the surface of the tooth and mechanical retention on the surface of the fastener.

In general, the gluing is done at the tooth or the dental prosthesis by chemical gluing, and on the side of the fastener by chemical gluing, if the coating is appropriate, or mechanical retention by grating or an appropriate retention surface.

Figure 7A:
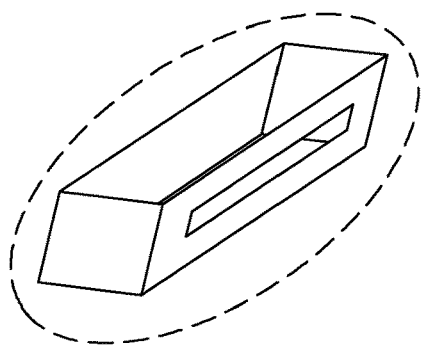
FIG. 7 shows a particular alternative of the preceding aspect.
Figure 7B:

FIG. 7 shows the detail of the fixing element of the single outer notch fastener type. It is made up of an element that may be summarily parallelepiped and wide enough to limit any mobility of the axis of the beam and of the beam itself, in rotation. The fastener has, on its face opposite the gluing surface, a fastening notch.

Figure 8A:
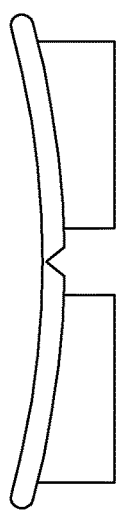
FIG. 8a shows another particular alternative of the preceding aspect of the disclosure in a top view.
Figure 8B:
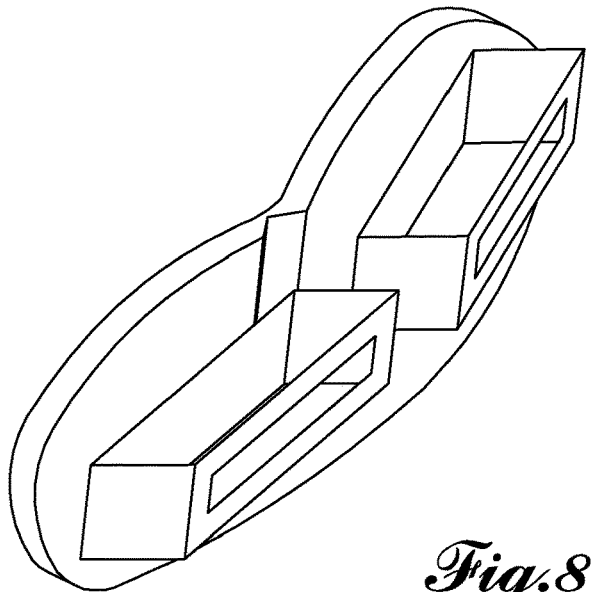
FIG. 8b shows another particular alternative of the preceding aspect of the disclosure in a side view.

FIG. 8 shows the detail of a fixing element of the double notch fastener type. In FIG. 8a, the element is seen from above, while in FIG. 8b, it is seen from the side (lateral-superior view). The gluing surface to the tooth is seen in its version having a weakness to facilitate loosening. The two parts of the double notch fixing type are seen placed on either side of the weak zone. By using a clamp to exert pressure on each side of the weak zone, the deformation of the gluing surface and loosening thereof are exerted.

Figure 9:
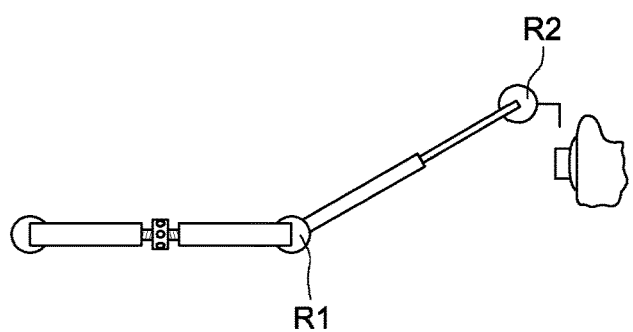
FIG. 9 shows a general view of the placement of a system according to the disclosure showing the preceding aspect.

FIG. 9 shows the placement of an arm in a patient's mouth, the jack being kept temporarily close to the palate. A fixing element present at the end of the arm interacts with a complementary fixing element glued to the tooth, to provide a clipping shape between the arm and the tooth. The ball joints R1 and R2 at both ends of the arm allow all of the elements to be positioned flexibly for a total adjustment of the device in the patient's mouth.

The operation is repeated for the various arms.

In FIG. 10, the central jack 23, also called base, is shown. It includes two identical elements that are rectangular rhombs, or half-bases 23a and 23b symmetrically facing one another relative to a general plane of symmetry of the system. The general plane of symmetry P of the system is meant to be placed globally on the general plane of symmetry of the patient's mouth in some situations, or otherwise so as to be off-centered in other situations, to obtain an asymmetrical application of the forces on either side of the jaw. The plane P is positioned according to the morphology and deformation of the patient, and to exert the necessary forces to resolve the deformation.

The two half-bases 23a and 23b are separated by a screw 24 operable by a key, which separates them or on the contrary brings them closer together on either side of the plane of symmetry. The screw 24 is surrounded by two shafts 25 and 26 that make it possible to keep the assembly made up of the two half-bases 23a and 23b rigid.

Figure 10A:
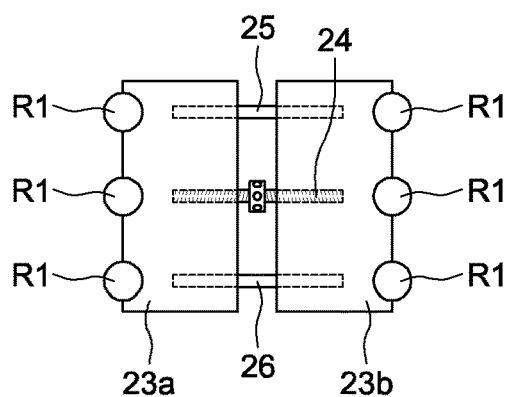
FIG. 10a shows a second aspect of the disclosure, made up of a jack bearing ball joints in a top or bottom view.
Figure 10B:
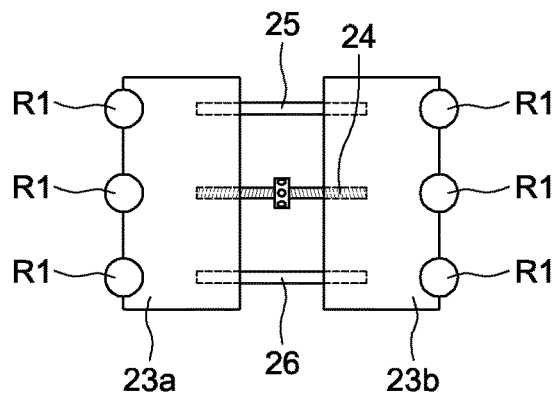
FIG. 10b shows a second aspect of the disclosure, made up of a jack bearing ball joints in a top or bottom view.
Figure 10C:
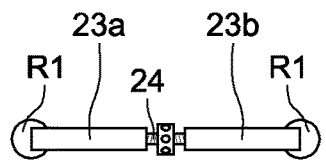
FIG. 10c shows a second aspect of the disclosure, made up of a jack bearing ball joints in a front view.

FIGS. 10a and 10b show the jack in top or bottom view, whereas FIG. 10c shows the jack in front view. FIG. 10a shows the jack 23 in a fairly closed position, while FIG. 10b shows, from the same angle, the jack 23 in a fairly open position. In the various views, one can see the six ball joints R1, three of which are fastened to the first half-base 23a, and the other three of which, symmetrical to the first three relative to the plane P, are fastened to the second half-base 23b. These six ball joints R1 make it possible to connect the jack to the six arms (not shown).

Figure 11A:
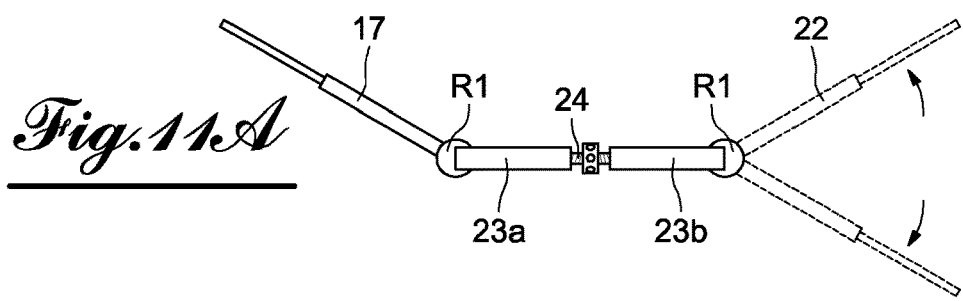
FIGS. 11a-11d show the degrees of freedom of arms around the base.
Figure 11B:
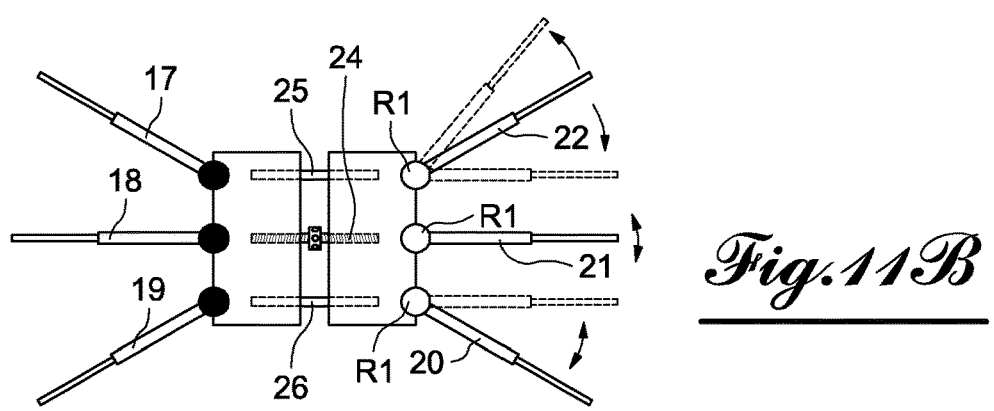
Figure 11C:
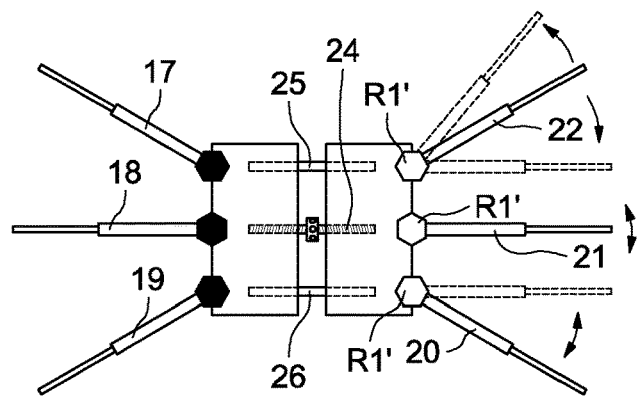

FIGS. 11a to 11d show the degrees of freedom of the arms 17 to 22 around the base in the vertical and anterior-posterior directions. FIG. 11a shows the vertical adjustment, while FIGS. 11b and 11c show the anterior-posterior adjustment.

FIG. 11a shows the base from the front. The figure is in a plane parallel to a plane including two ball joints R1 connecting the base and the two arms 18 and 21, while being parallel to the screw 24, but perpendicular to the plane formed by the screw 24 and the shafts 25 and 26. A rotation of the arm is shown around an axis perpendicular to the plane of the figure. This is the arm 21, shown coplanar with the screw 24.

In FIG. 11b, which shows the base from above, the figure being in a plane parallel to the plane formed by the screw 24 and the shafts 25 and 26, rotations of the arm are shown around an axis perpendicular to the plane of the figure. This involves the arms 20, 21 and 22 shown coplanar with the screw 24 and the shafts 25 and 26.

Figure 11D:
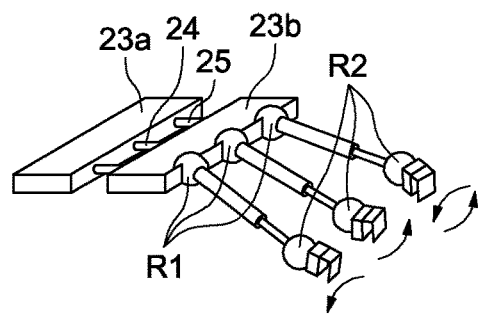

The third degree of rotational freedom around the ball joint R1, which corresponds to a rotation around the axis of the arms 17 to 22, may be present or absent (FIG. 11d). The mechanical rotation connections R1 are then chosen from among complete ball joint connections (three degrees of rotation), finger ball joint (two degrees of rotation, viewed in FIGS. 11a to 11c), or even in a simpler version, a pivot (one single degree of rotation, chosen from among the two degrees of rotation shown in FIGS. 11a to 11c).

The rotations shown above may be continuous.

In FIG. 11c, a version is shown in which the ball joints R1 are replaced by links R1' allowing a discrete adjustment of an angle. This can be done by a system of polygonal and regular complementary shapes to be embedded. The illustrated example is hexagonal. The system may be used over one, two or three degrees of rotational freedom, in which case it uses an embedding of polyhedral shapes.

Figure 12A:
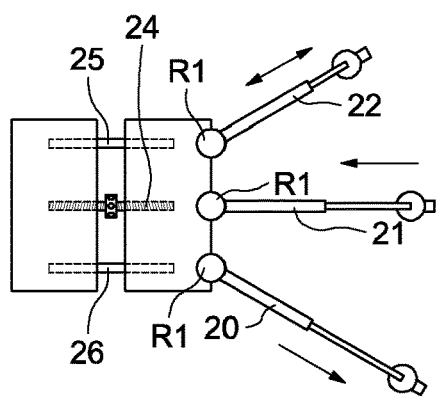
FIGS. 12a-12c show a second important property of a system according to the disclosure, in connection with a fourth aspect of the disclosure, made up of a telescoping beam.

In FIGS. 12 (12a, 12b and 12c), the degrees of freedom are shown of the arms regarding lengthwise extension. The transverse direction is in fact managed by the telescoping aspect of each of the beams. In FIG. 12a, the view is the same as in FIG. 11: the extension of the arms 20, 21 and 22 is shown, which are retractable or telescoping arms, the total length of which can be adjusted, independently for each arm.

Figure 12B:
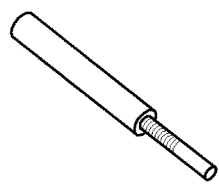

In FIG. 12b, an example embodiment of a telescoping arm is shown: this is a system including two arm parts, one made up of a wide hollow cylinder of an empty inner cylinder emerging over a straight section, the other made up of a thin cylinder inserted into the empty cylinder of the first part. The two parts cooperate by screwing, or alternatively by a wedging system by notches cooperating with one or several teeth, the screw pitches, or the notches and the teeth being borne by mutual contact surfaces of the two cylinders. The amplitude of the screwing movement or the choice of the notch or the tooth used for the wedging makes it possible to adjust the length of the arm.

Figure 12C:
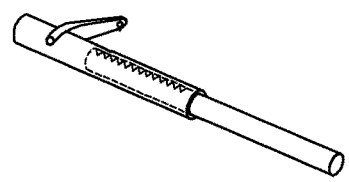

In FIG. 12c, another example embodiment of the telescoping arm is shown: this again involves a system with two arm parts, like the previous one. The two parts are immobilized relative to one another by an outer gate that pivots relative to one of the two parts and engages a notch from among a plurality of notches borne by the outer surface of the other part. The choice of the notch makes it possible to adjust the length of the arm.

Alternatively, the arms or beams have fixed lengths, and the length adjustment is done at the central jack or at the ball joints.

In FIGS. 13 (13a to 13c), the degrees of freedom of the arms are shown with respect to the fixing systems to the teeth, or if one prefers, expressed differently, the freedom of orientation of the head of each arm with respect to the arm to allow the orientation of the fasteners that must adapt to the teeth and to their orientation. The arm shown, for example, is the arm 21. The arm 21 ends at its end connected to the jack 23 by a ball joint R1 and at its other end by a ball joint R2. The ball joint R2 articulates the arm 21 with a fixing element 30 to be fixed to a complementary element fixed beforehand to a tooth, like those shown in FIGS. 6 to 8.

Figure 13A:
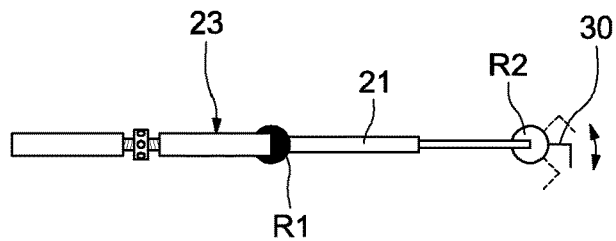
FIGS. 13a and 13b show a third important property of a system according to the disclosure, in connection with a fifth aspect of the disclosure, made up of a fastening element rotating with respect to a beam showing two planes perpendicular to each other, both parallel to an arm.
Figure 13B:
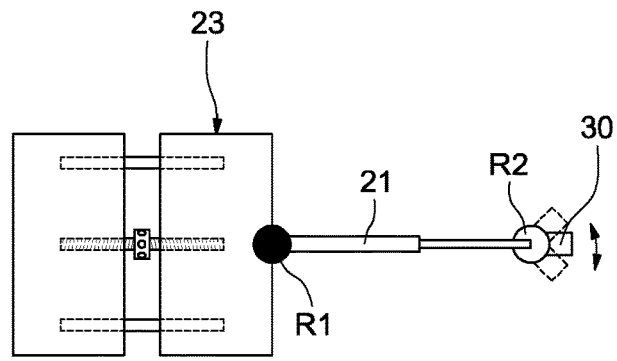

In FIGS. 13a and 13b, views are shown in two planes perpendicular to one another, both parallel to the arm 21. In order to simplify the explanation, the device is shown with all other things being equal, the ball joint R1 is kept frozen between the two views, which is symbolized by the shading in black in the figure. In particular, the jack 23 keeps the same separation between the two views. In FIG. 13a, the jack is seen from the front, the plane of the figure being perpendicular to the plane defined by the screw 24 and the shafts 25 and 26, while in FIG. 13b, the jack 23 is seen from the top, in a plane parallel to the screw 24 and the shafts 25 and 26.

As can be seen in the two FIGS. 13a and 13b, the fixing element 30 can rotate in two dimensions of the space with respect to the arm 21, around two axes each parallel to the plane of FIG. 13a and FIG. 13b, respectively.

Figure 13C:
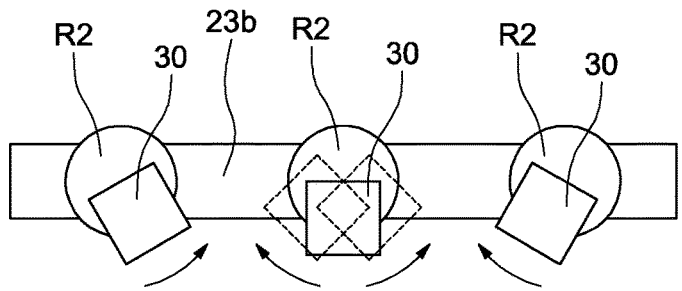
FIG. 13c shows a third important property of a system according to the disclosure, in connection with a fifth aspect of the disclosure, made up of a fastening element rotating with respect to a beam, with a pivot option.

The third degree of rotational freedom around the ball joint R2, which corresponds to a rotation around the axis of the arm 21, may be present or absent, although it is preferably interesting for it to be present. The mechanical rotational links R2 are thus chosen from among complete ball joints, finger ball joints, or even in a simpler pivot version (FIG. 13c).

The adjustment at the ball joints R2 is very useful to allow the adjustment of the system. The latter must initially be flexible enough to be able to be placed in the mouth precisely in its final place, while remaining passive, i.e., not applying any force on the teeth, gums and palate. The device is next activated by rotation of the screw of the jack, and begins its action from the position in the configuration in which it was initially installed.

The rotation at the ball joint R2 can be continuous, with a mechanical, or discreet, link with a polygon or polyhedron embedding system, as mentioned with the rotation R1.

Figure 14:
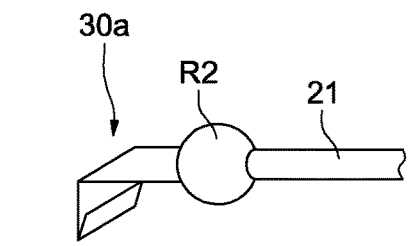
FIG. 14 shows a sixth aspect of the disclosure, made up of fixing by clipping, tooth by tooth.

FIG. 14 shows a fixing element as introduced in connection with the preceding figure, namely the fixing element 30 placed at the end of an arm opposite the jack. Here it is denoted fixing element 30a. An arm, for example the arm 21, is visible, as well as the associated ball joint R2. The fixing element to the tooth is a single outer notch fastener 101. It interacts, by clipping-type embedding, with a hook shape of the fixing element 30. The fixing element 30 is supported by the ball joint R2 and in rotation owing to the latter, with the arm 21.

Figure 15:
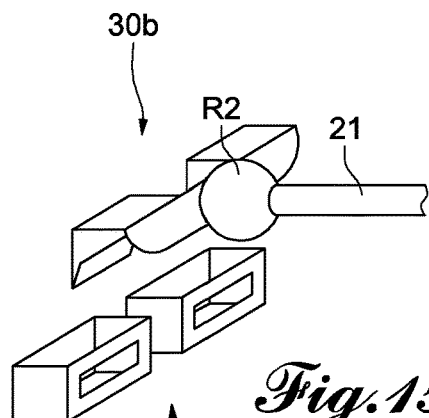
FIG. 15 shows the same aspect, in one alternative.

FIG. 15 shows another fixing element as introduced in connection with the preceding figure, namely the fixing element 30 placed at the end of an arm opposite the jack. Here it is denoted fixing element 30b. An arm, for example the arm 21, is visible, as well as the associated ball joint R2. The fixing element to the tooth is a double outer notch fastener 103. It interacts, by embedding of the clipping type, with a double hook shape of the fixing element 30b, to increase the stability.

The fixing element 30b is supported by the ball joint R2 and in rotation owing to the latter, with the arm 21.

Figure 16A:
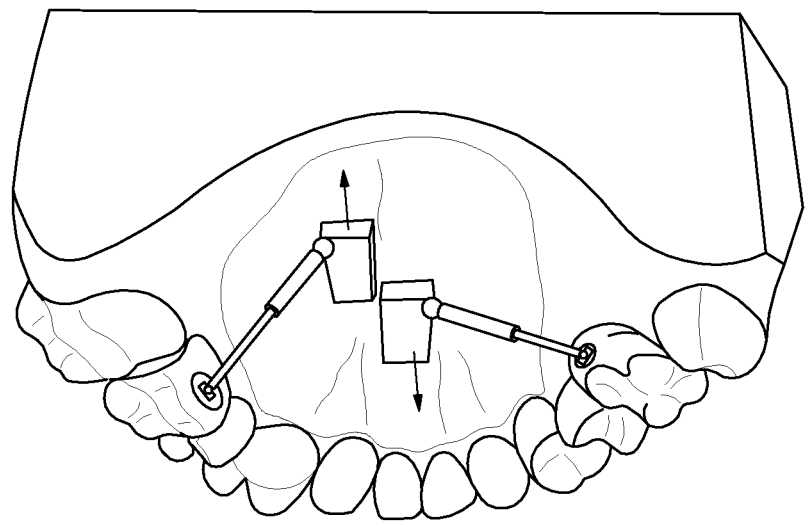
FIG. 16a shows a possible adjustment of the system according to the disclosure, showing an anterior-posterior adjustment of the base, made possible owing to the various discussed aspects.
Figure 16B:
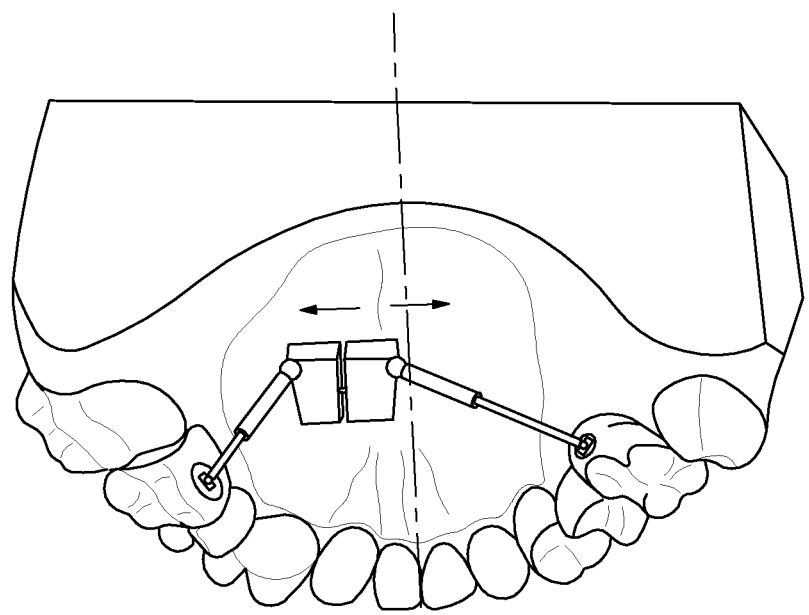
FIG. 16b shows a possible adjustment of the system according to the disclosure, showing a transverse adjustment plane of the base, made possible owing to the various discussed aspects.
Figure 16C:
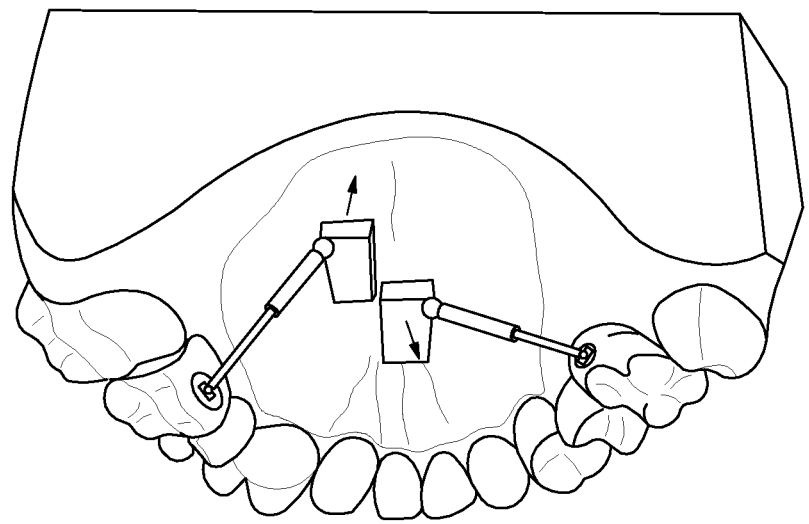
FIG. 16c shows a possible adjustment of the system according to the disclosure, showing a height adjustment of the base, made possible owing to the various discussed aspects.

FIGS. 16a to 16c show the modes for adjusting the palate expansion system 10 in a patient's mouth.

FIG. 16a shows the anterior-posterior adjustment of the base, which can be moved from the bottom of the mouth toward the front of the mouth, along the hard palate, while remaining in the horizontal plane (for discussion, it will be specified that irrespective of the position of the patient, the horizontal plane is the anatomical horizontal plane).

FIG. 16b shows the transverse adjustment plane of the base, which may be moved from the center of the palate toward the left of the palate or toward the right of the palate.

FIG. 16c shows the height adjustment of the base, which may be moved upward (i.e., in the context of a vertical or sagittal adjustment, or vertical adjustment of the distance of the base of the device with the hard palate), i.e., toward the top of the palate or downward, i.e., toward the center of the mouth (the patient standing upright).

Figure 17:
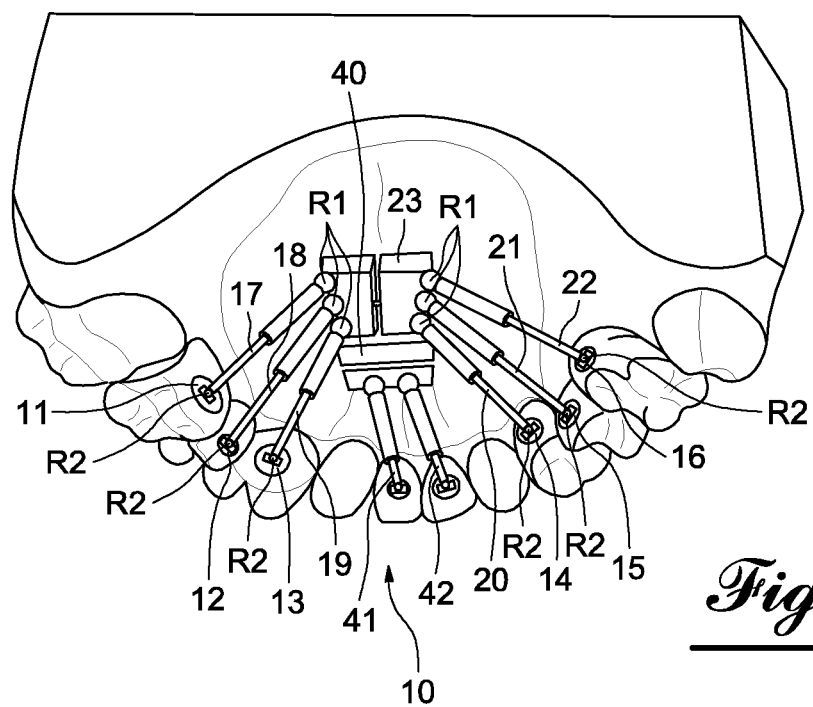
FIG. 17 shows one possible option for the system according to the disclosure.

FIG. 17 shows an embodiment of the palate expansion system 10a offering an additional action mode that allows it an action on other palate sutures. In addition to the elements described above, it offers a second base comprising a second screw performing a second function of the jack, for example to act on the incisor sutures of the palate. Here, we have shown the jack 23 and the arms 17 to 22. Added to these elements is the jack 40, the expansion direction of which is approximately perpendicular to the expansion direction of the jack 23. Said jack 40 supplies an adjusting separating force between the jack 23 and the incisors. Two arms 41 and 42 are shown between the jack 40 and the incisors. Ball joints can advantageously be present at one or the other of the ends of said arms, or at both ends. One screw of the jack 40 provides the separation between two arms 41 and 42 and the jack 23, placed opposite them relative to the jack 40.

This alternative makes it possible to act to widen the palate in different directions, by using different movements, to act on bone sutures other than the central suture of the sagittal plane. Other arrangements using different movements can be considered, based on the patient's needs, to resolve his pathologies.

The device may also include or be used with bone bearing means. It is then possible to use specific bearing means to be screwed through the gingival mucosa in the bone of the palate, through an additional module allowing the junction with many anchoring screws or osteosynthesis plates (adjusted on the gingiva), or bone anchoring implants.

Figure 18:
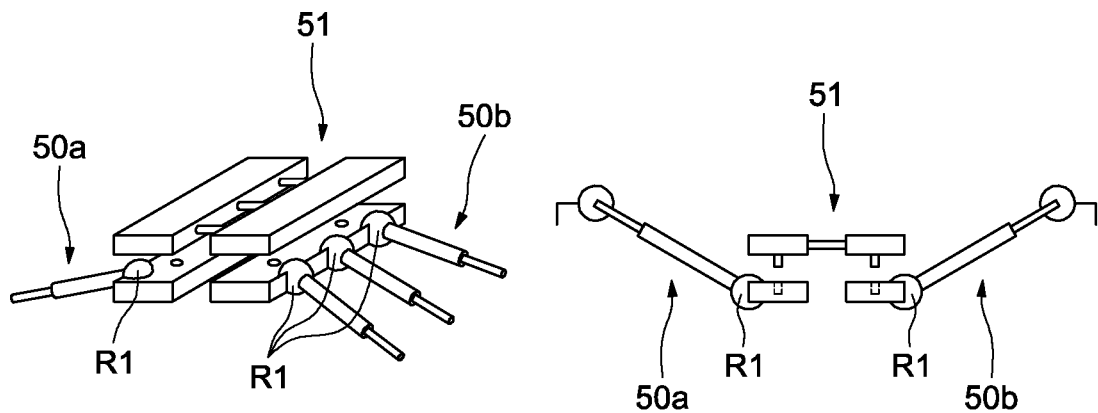
FIG. 18 shows another possible option for the system according to the disclosure.

FIG. 18 shows one particular embodiment of the base, in which three separate elements are fixed to one another to facilitate the manufacture or installation. The palate expansion system 10b includes two sets of three arms 50a and 50b, the three arms of each set being connected to one another by a shared pedestal to which they are articulated by the ball joints R1. An independent jack is fixed by embedding or any other means to the two sets of three arms 50a and 50b, therefore connecting them. The controlled expansion elements of the jack (screw and shafts, for example) are placed so as to allow the control of the distance between the set of three arms 50a and the set of three arms 50b.

Figure 19:
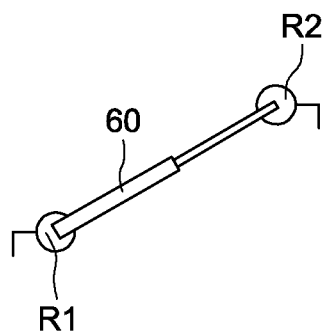
FIG. 19 shows still another possible option for the system according to the disclosure.

FIG. 19 shows one particular embodiment of an arm for the palate expansion system according to the disclosure. This arm 60 has, at each end, a ball joint R1 or R2, but is removable relative to the base and the jack. It may be fastened to the base using a fastening element by clipping supported by the ball joint and in rotation relative to the arm or any other means borne by the ball joint and in rotation with respect to the arm, interacting with a complementary means borne stationary by the base. Alternatively, in the case of such a removable arm, the ball joint R1, instead of being borne by the arm, may be borne by the base, the fixing element by clipping of the base being borne by the ball joint and interacting with a complementary element borne stationary by the arm. In any case, the clipping involves a form of locking.

The device may be used in infantile, adolescent or adult human dental-facial orthodontics or orthopedics, and optionally in a similar use for animals.

The placement of the system includes gluing fasteners on the teeth, positioning the base in the palate, clipping the beams, adjusting the position and locking the ball joints.

The disclosure is not limited to the described embodiments, but encompasses all alternatives within the scope of the claims also in removable devices (able to be removed by the patient) and not glued, or fixed, sealed or glued devices (only able to be removed by the practitioner).

It will be specified that the mechanisms and elements of the described kit may be associated with elements manufactured by CAD/CAM (computer-assisted design/computer-assisted manufacturing).

The entire device may be provided in a kit, i.e., a set of prefabricated elements that makes it possible to place an orthodontic palate expander or distraction device that is completely adapted and fitted to the patient.

It is provided that these devices have added plates or trays (plates with slot) manufactured by CAD/CAM belonging to a 3D chain for the digital acquisition of the oral cavity to be printed by 3D printer using resin, a composite material or metal through an additive or subtractive (grinding) method. The device can thus be used with elements prefabricated by CAD/CAM or another method such as plates or trays fitted to the dental and/or palatal morphology.

If plates or trays are used, the device is easily removable for the patient. Otherwise it is fixed, in that only the specialized practitioner is able to remove it.

Mini-screws and orthodontic anchoring implants may also be associated with the device.

In one configuration of the system, it is possible to make adjustments outside the mouth, and even outside the chair. A traditional imprint (with a material of the alginate or silicone type) or an optical (digital) imprint makes it possible to determine the necessary adjustments, and the adjustment can be done in advance without an immediate need for the patient to be present. An internal or external device is also provided in order to perform the necessary settings and adjustments in advance.

Lastly, when the device is provided for palatal expansion, it may also widen the real or artificial mandibular sutures (created in this case by surgery). The functions described for this device allow it also to perform unitary or multiple dental movements, whether simultaneous or sequential.

The invention claimed is:

1. An orthodontic device, comprising:
a first set of first beams, configured to bear on respective first teeth of a left side of a jaw of a patient to be treated;
a second set of second beams configured to bear on respective second teeth of a right side of said jaw; and
one central jack for modulating a separation of said first set of beams and second set of beams,
first angular adjustment mechanisms, each disposed between the central jack and a respective first beam of said first set of beams and second angular adjustment mechanisms, each disposed between the central jack and a respective second beam of said second set of beams to allow a geometric adjustment of the device at least in the vertical direction or the anterior-posterior direction during a placement of the device in the patient's mouth, wherein the first angular adjustment mechanisms and the second angular adjustment mechanisms each comprise joint balls.

2. The orthodontic device according to claim 1, wherein at least one of the first and second sets of beams is adjustable lengthwise to further allow the geometric adjustment of the device in the transverse direction during a placement of the device in the patient's mouth.

3. The orthodontic device according to claim 1, wherein at least one of the beams of the first or second sets can be disassembled, the device including at least one replacement beam with a different length to allow the geometric adjustment of the device during a placement of the device in the patient's mouth.

4. The orthodontic device according to claim 1, further comprising a rotating mechanical link at the end opposite the central jack of each of the first beams and second beams, to be inserted between the respective beam and the jaw.

5. The orthodontic device according to claim 1, further comprising fasteners configured to be secured to the teeth, and bearing connectors configured to connect the fasteners to the respective beam, the device additionally including complementary connecting elements connected to the respective beam to place the device in the patient's mouth using fasteners.

6. The orthodontic device according to claim 5, including fasteners bearing single outer notches, double outer notches or an outer ball for a nesting connection, or screwing elements for a screwing connection.

7. The orthodontic device according to claim 1, wherein the central jack is fixed on a left support and on a right support that are free relative to one another.

8. A method for placing an orthodontic device, comprising:
   placing first bearings of a set of first bearings for the device on respective teeth of a left side of an upper jaw of a patient to be treated;
   placing second bearings of a set of second bearings for the device on respective teeth of a right side of said jaw,
   placing respective first beams between one central jack of the device and first bearings of the first set of first bearings and second beams between said central jack and second bearings of the set of second bearings; and
   adjusting an angle between the central jack and at least one of said first beams, or an angle between the central jack and at least one of said second beams to adjust a geometry of the device, at least in the vertical direction or the anterior-posterior direction,
   wherein each of said adjusting an angle includes adjusting a respective joint ball.

9. The method for placing an orthodontic device according to claim 8, further comprising placing the orthodontic device to perform single or multiple dental movements.

* * * * *